(12) United States Patent
Zhang et al.

(10) Patent No.: US 9,207,165 B2
(45) Date of Patent: Dec. 8, 2015

(54) SAMPLE CHAMBER FOR LASER ABLATION ANALYSIS OF FLUID INCLUSIONS AND ANALYZING DEVICE THEREOF

(71) Applicants: China Petroleum & Chemical Corporation, Beijing (CN); SINOPEC Exploration & Production Research Institute, Beijing (CN)

(72) Inventors: Zhirong Zhang, Beijing (CN); Tenger, Beijing (CN); Dan Rao, Beijing (CN); Weijun Shi, Beijing (CN); Qigui Jiang, Beijing (CN); Jianzhong Qin, Beijing (CN); Qu Zhang, Beijing (CN); Binbin Xi, Beijing (CN)

(73) Assignees: CHINA PETROLEUM & CHEMICAL CORPORATION, Beijing (CN); SINOPEC EXPLORATION & PRODUCTION RESEARCH INSTITUTE, Beijing (CN)

( * ) Notice: Subject to any disclaimer, the term of this patent is extended or adjusted under 35 U.S.C. 154(b) by 486 days.

(21) Appl. No.: 13/656,492

(22) Filed: Oct. 19, 2012

(65) Prior Publication Data

US 2013/0125674 A1 May 23, 2013

(30) Foreign Application Priority Data

Oct. 19, 2011 (CN) .......................... 2011 1 0319046

(51) Int. Cl.
  *G01N 15/14* (2006.01)
  *G01N 21/03* (2006.01)
  *G01N 33/24* (2006.01)
  *G01N 21/71* (2006.01)
  *G01N 1/04* (2006.01)

(52) U.S. Cl.
  CPC ............ *G01N 21/0332* (2013.01); *G01N 21/03* (2013.01); *G01N 21/718* (2013.01); *G01N 33/241* (2013.01); *G01N 2001/045* (2013.01); *G01N 2021/0389* (2013.01)

(58) Field of Classification Search
  None
  See application file for complete search history.

(56) References Cited

U.S. PATENT DOCUMENTS

| 4,193,963 | A | * | 3/1980 | Bruening et al. | ............... 422/52 |
| 5,120,129 | A | * | 6/1992 | Farquharson et al. | ........ 356/246 |
| 7,335,164 | B2 | * | 2/2008 | Mace et al. | .................... 600/532 |
| 8,586,943 | B2 | * | 11/2013 | Verbeck et al. | ................ 250/429 |
| 2006/0132761 | A1 | * | 6/2006 | Hall | ............................... 356/244 |
| 2007/0248493 | A1 | * | 10/2007 | Baehr | ............................. 422/78 |
| 2011/0042564 | A1 | * | 2/2011 | Naito et al. | .................... 250/287 |
| 2012/0099103 | A1 | * | 4/2012 | Hahn | ............................. 356/316 |
| 2012/0135537 | A1 | * | 5/2012 | Horton et al. | ................. 436/172 |

* cited by examiner

*Primary Examiner* — Robert R Raevis
(74) *Attorney, Agent, or Firm* — Novick, Kim & Lee, PLLC; Allen Xue

(57) ABSTRACT

The present invention relates to a sample chamber for laser ablation analysis of fluid inclusions, comprising a sample cell having a sample cell through-hole extending along the vertical direction and a sample channel extending through the sample cell in a direction transverse to the vertical direction and communicating with the sample cell through-hole. A transparent element is arranged on each of the top and bottom sides of the sample cell through-hole, and is fixed to the sample cell through a fixing ring. The sample chamber further comprises a base comprising a viewing hole and a receiving portion for receiving the sample cell, wherein the viewing hole is coaxially aligned with the sample cell through-hole when the sample cell is placed within the receiving portion. According to the sample chamber of the present invention, it is only necessary to change the sample cell during replacement of the sample chamber, which leads to a convenient operation. At the same time, light from the microscope can pass through the viewing hole, so that the effect of observation is improved.

14 Claims, 2 Drawing Sheets

SAMPLE CHAMBER FOR LASER ABLATION ANALYSIS OF FLUID INCLUSIONS AND ANALYZING DEVICE THEREOF

CROSS REFERENCE TO RELATED APPLICATION

This application claims priority to Chinese Patent Application No. CN 201110319046.6 filed on Oct. 19, 2011, which hereby is incorporated herein in its entirety.

TECHNICAL FIELD

The present invention relates to the field of oil exploration, in particular relates to a sample chamber for laser ablation analysis of fluid inclusions and a device for laser ablation analysis of fluid inclusions which comprises the above-mentioned sample chamber.

BACKGROUND

It is well know that fluid inclusion is a kind of sample reserved in geological body during the formation of rocks, minerals, deposits and so on. The fluid inclusion can provide various kinds of information, such as the formation conditions of rocks and minerals, and the storage, migration and evolution of oil and natural gas and the like.

Oil-bearing fluid inclusions generally exist in the samples of sedimentary rocks. Once the oil/gas components in the fluid inclusion are entrapped, they will be reserved in a relatively closed space, and thus can be prevented from alteration effects at later stages, such as biodegradation, water washing and the like. Therefore, the hydrocarbon components in the oil-bearing fluid inclusions can provide the information of original oil/gas composition when captured. The analysis results of oil-bearing fluid inclusions can be directly used in the study on oil source correlation, hydrocarbon migration and the like.

However, fluid inclusions are generally extremely small, and in particular the oil-bearing fluid inclusions have a diameter generally not greater than 20μm. As a result, the techniques for analyzing the composition of fluid inclusion are very challenging, and the sample chamber is crucial in the process of analyzing fluid inclusion by laser ablation.

CN201010521367 discloses a device for isotope analysis of micro-minerals by laser ablation. As shown in FIG. 1, the device includes a sample chamber 300 for laser ablation, and the sample of fluid inclusion can be observed with a microscope via reflected light and thus be analyzed by laser ablation. As shown, the sample chamber 300 comprises a chamber body 307, within which a sample cell is arranged. The sample chamber 300 further comprises a quartz glass plate 303, which is fixed on the upper end of the chamber body 307 through a cover plate 305 and screws 302. For preventing leakage, an O-ring 304 can be further arranged between the quartz glass plate 303 and the chamber body 307. A horizontal gas carrying channel 308 penetrating through two opposite sides of the chamber body is formed inside the chamber body 307, and both ends of the gas carrying channel 308 are connected to outer pipelines with ferrule joints 301 and 306 respectively. In this manner, the carrier gas can pass through the gas carrying channel 308 and sweep the sample in sample chamber. The substances generated enter into a detector through the outer pipelines connected with the joint 306, and then can be analyzed by the detector.

However, the sample chamber 300 still has some defects. For example, the sample chamber cannot be observed through transmitted light, which is crucial for the observation of fluid inclusions. In addition, the sample chamber cannot be heated up in a short time, which enables the whole analyzing process relatively long. Also, the whole sample chamber has to be replaced in case of a breakdown, which needs to shut down the whole device during replacement, thus causing an inconvenient operation.

SUMMARY OF THE INVENTION

According to the first aspect of the present invention, a sample chamber for laser ablation analysis of fluid inclusions is provided, which comprises: a sample cell having a sample cell through-hole extending along the vertical direction and a sample channel extending through the sample cell in a direction transverse to the vertical direction and communicating with the sample cell through-hole, wherein a transparent element is arranged on each of the top and bottom sides of the sample cell through-hole, and is fixed to the sample cell through a fixing ring; and a base comprising a viewing hole and a receiving portion for receiving the sample cell, wherein the viewing hole is coaxially aligned with the sample cell through-hole when the sample cell is placed within the receiving portion.

According to the present invention, said sample cell is made from a first material and said base is made from a second material, wherein the density of the second material is less than that of the first material, and/or the coefficient of heat transfer of the second material is greater than that of the first material. Preferably, said first material is stainless steel and said second material is aluminum.

In one example, a heating device is arranged inside said base. In particular, said heating device comprises a heating rod extending along a direction orthogonal to both of the sample cell through-hole and the sample channel In the sample chamber of the present invention, said base is further provided with a thermocouple which is arranged orthogonal with the heating rod.

In a preferred example, the transparent element is quartz glass plate. In addition, a sealing element is arranged between said transparent element and the sample chamber. The sealing element is preferably a fluoro-rubber O-ring.

In the sample chamber of the present invention, said receiving portion can be one selected from a group consisting of step, through groove, and recess.

In the sample chamber of the present invention, on said sample cell or on said base a locating device is arranged, with which the viewing hole of the base can be coaxially aligned with the sample cell through-hole.

In the sample chamber of the present invention, both of the sample cell and the base are shaped as a cuboid. And when the sample cell is mounted on the base, the sample cell and the base together form a whole cuboid.

In the sample chamber of the present invention, the diameter of said viewing hole is equal to or greater than that of said sample cell through-hole.

In a preferred example of the present invention, threaded ferrules are arranged at both ends of said sample channel for connecting with outer sample pipelines.

Further, a hollow cylinder can be placed in said sample cell through-hole, wherein the external diameter of the hollow cylinder matches with the inner diameter of the sample chamber.

According to the second aspect of the present invention, a device for laser ablation analysis of fluid inclusions is provided, which comprises the sample chamber according to the first aspect of the present invention.

In the present invention, the sample chamber is designed as having a split-type structure, i.e., having a sample cell and a base that are separated from each other. Therefore, during replacement of the sample chamber, it is only necessary to change the sample cell, which leads to a convenient operation. As the sample cell and the base are separated from each other, they can be designed respectively, such that the base with a greater volume can be made from lighter material for reducing the mass of the sample chamber as a whole. At the same time, the coefficient of heat transfer of the material of the base is selected as being greater than that of the material of the sample chamber. Therefore, the heat transfer efficiency of the whole sample chamber is improved, which in turn increases the heating rate. Further, a viewing hole is arranged in the base. In this case, light from the microscope can pass through the viewing hole, so that the effect of observation is improved.

BRIEF DESCRIPTION OF THE DRAWINGS

The present invention will now be described in detail with reference to the accompanying drawings. However, it should be noted that the drawings are provided only for better understanding of the present invention, and therefore should not be construed as restrictions to the invention in any way. In the drawings.

DETAILED DESCRIPTION OF THE EMBODIMENTS

Figure 1:
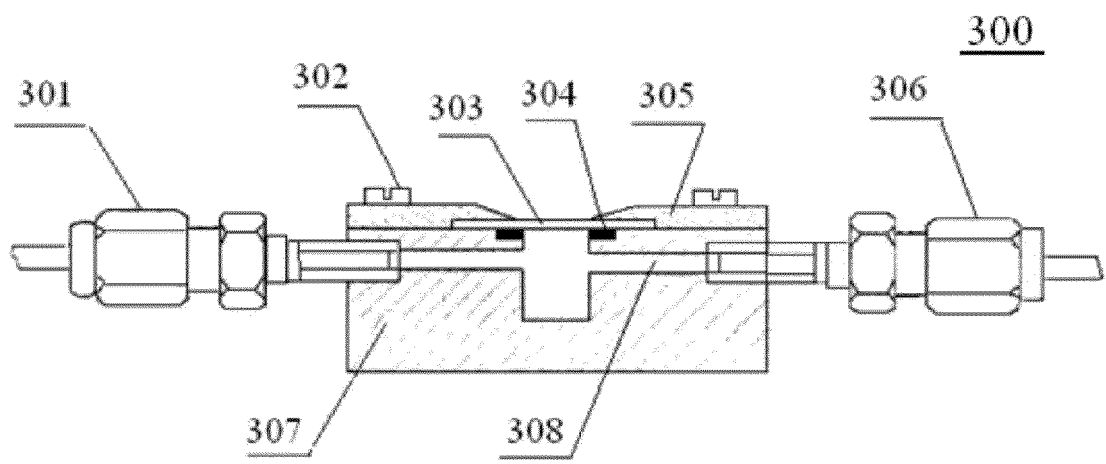
FIG. 1 schematically shows the structure of a sample chamber in the prior art.
Figure 2:
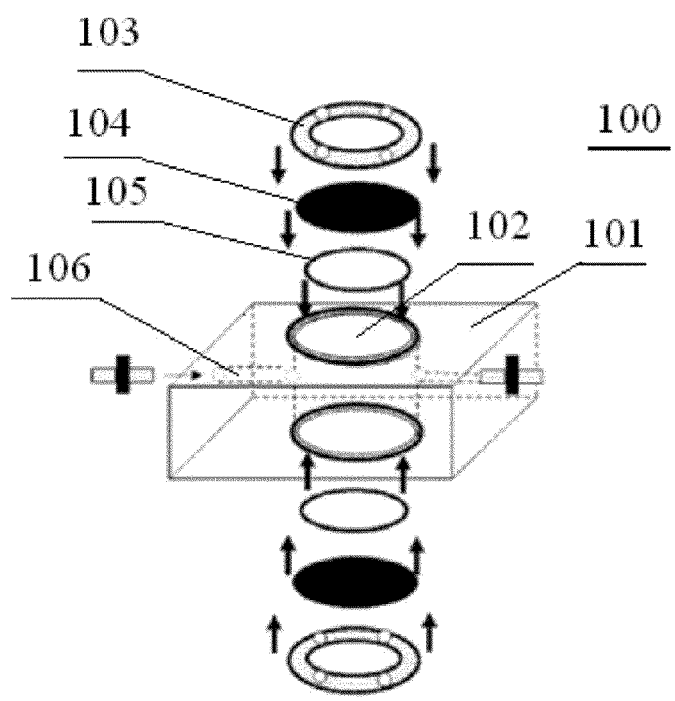
FIG. 2 schematically shows the explosive view of the structure of the sample chamber of the sample chamber according to the present invention.

In the following a specific embodiment of the present invention will be discussed with reference to FIGS. 2 and 3.

The sample chamber according to the present invention comprises a sample cell 100 and a base 200 that are separated from each other. As shown in FIG. 2, the sample cell 100 is preferably shaped as a cuboid, and comprises a sample cell through-hole 102 extending along the vertical direction. The sample cell through-hole 102 is preferably located at the center of the sample cell 100. A sample channel 106, which communicates with the sample cell through-hole 102, extends through two opposite sides of the sample cell 100 in a direction transverse to the direction along which the sample cell through-hole 102 extends. Preferably, the sample channel 106 extends along the horizontal direction. In a particular example, threaded ferrules of ⅛ inch made of stainless steel are arranged at both sides of the sample channel 106, in order to connect the sample channel 106 with gas carrying pipelines for transfer of the sample. Thus the fluid carrying the sample can be introduced into the sample cell through-hole 102 via the sample channel 106, and analyzed therein.

According to the embodiment of the present invention, a transparent element 104, which is preferably quartz glass plate, is arranged on each of the top and bottom sides of the sample cell through-hole 102. Laser can pass through the quartz glass plate, and thus focus on the surface of the sample. The transparent elements 104 are fixed to the sample cell 100 with respective fixing rings 103. In an optional embodiment, a sealing element 105, which is preferably a fluoro-rubber 0-ring, is arranged between the transparent element 104 and the sample cell 100. The fixing rings 103 can be secured to the sample cell through-hole 102 by means of fixing elements, such as four bolts, so that the sample chamber can be sealed.

According to the present invention, the sample chamber for accommodating the sample to be analyzed can be in a form of through-hole, and transparent elements (i.e., quartz glass plates) are arranged on both sides of the through-hole. In this way, the laser and the viewing light can be introduced into the sample chamber from the top side and the bottom side respectively, thus on one hand improving the efficiency of laser ablation and on the other hand significantly increasing the effect of observation.

Figure 3:
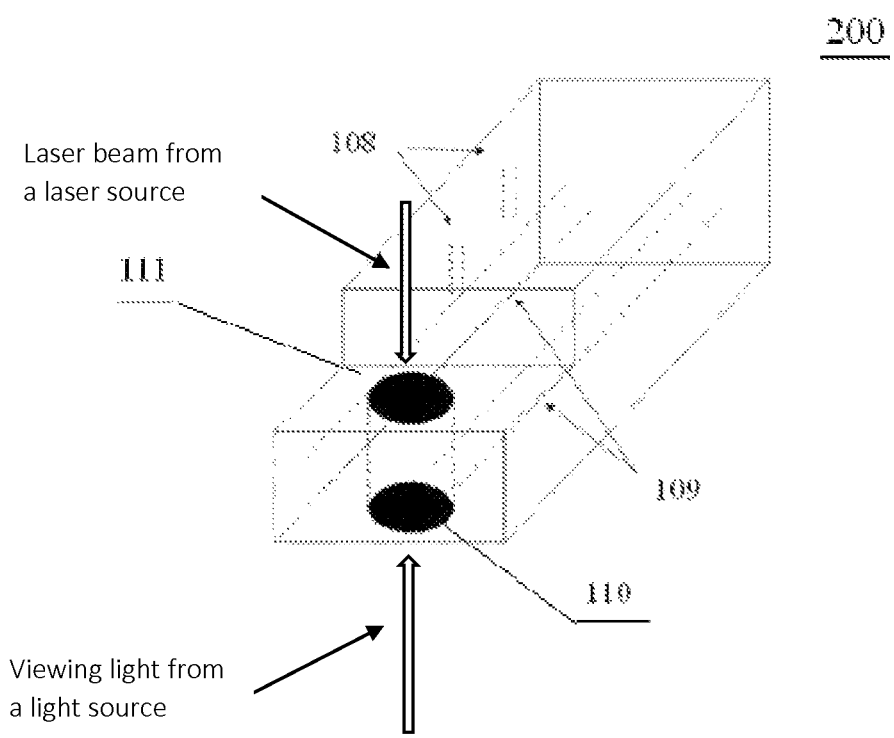
FIG. 3 schematically shows the structure of the base of the sample chamber according to the present invention.

As illustrated in FIG. 3, the base 200 according to the present invention can be made into various shapes, preferably a cuboid. The base 200 comprises a viewing hole 110 extending along the vertical direction and a receiving portion 111 for receiving the sample cell 100 therein. The size and shape of the receiving portion 111 can be determined according to the sample cell 100, and can be one of step, through groove and recess. The base 200 can be envisaged so that when the sample cell 100 is placed within the receiving portion 111, the viewing hole 110 is coaxially aligned with the sample cell through-hole 102. Thus it is possible to observe the sample positioned in the sample cell through-hole 102 through the transparent elements 104 via the viewing hole 110.

According to the sample chamber of the present invention, in use the inclusion sample is placed in the sample cell 100, and the sample cell 100 can be placed onto the base 200 after being sealed. The sample channel 106 is connected to an on-line analysis gas carrying pipeline system. The base 200 can be heated with heating rods, and the temperature value is sent back to a temperature controller by the thermocouple. The laser can pass through the transparent elements 104 effectively, and focus on the surface of the sample for ablation.

According to the sample chamber of the present invention, the sample cell 100 is made from a first material and the base 200 is made from a second material, wherein the first material is selected as having a density greater than the second material. In this way, the base 200 with a larger volume can be made with lighter material, thus reducing the mass of the sample chamber as a whole and enabling the microscope stage hard to be damaged. Alternatively or additionally, the second material can be selected as having a coefficient of heat transfer greater than the first material. In this way, the heat transfer efficiency of the whole sample chamber can be improved, and the heating rate can be increased also. As a preferred example, the first material is stainless steel and the second material is aluminum.

According to the present invention, in order to improve the heating rate of the sample chamber and accelerate the analysis process, a heating device and a temperature sensing device are provided in the base 200. In the example illustrated in FIG. 3, the heating device comprises two heating rods, and the temperature sensing device comprises two thermocouples. It can be easily understood that the quantity of the heating rods and the thermocouples can be selected as needed. Preferably, the heating rods are arranged within two heating rod holes 109 provided in the base 200 along the longitudinal direction, and the thermocouples are arranged within two thermocouple holes 108 provided in the base 200 along the vertical direction. Preferably, the heating rod holes 109 can be orthogonal to both of the viewing hole 110 and the sample channel 106.

Tests show that the device including the sample chamber for laser ablation analysis of fluid inclusions according to the present invention can detect the composition of hydrocarbon substances ranging within the scope of C4-C30 in terms of monomer fluid inclusion analysis. The scope of monomer fluid inclusion analyzing and detecting is improved compared with the current known scope C4-C20 that can be obtained from the conventional devices.

As known, the factors that will affect the detection range include the design of the sample chamber, the design of the transfer pipelines, the method adopted and the conditions for analyzing, etc. The sample chamber according to the present invention modifies the structure of current sample chambers, so that light can be transmitted through the sample chamber, thus improving the effect of observation. On the contrary, current sample chambers can only be observed with reflected light. In this case, the fluid inclusion can only be observed with fluorescence, and the fluid inclusion without fluorescence cannot be observed. At the same time, it is possible that other organic substances displaying fluorescence can be present in the sample, so that the determination of fluid inclusion will be easily adversely affected.

For reducing the dead volume of analyzing, according to the present invention, a hollow cylinder can be placed in the inner chamber of the sample chamber, i.e., inside the sample cell through-hole 102. In operation, the hollow cylinder with a certain wall thickness is placed into the sample chamber, such that the external diameter of the hollow cylinder matches with the inner diameter of the sample chamber. In this manner, the projecting light can still pass through the chamber, and the sample of small volume can be placed conveniently. For example, the sample can be placed directly on the cylinder, or on a piece of sheet glass which is placed on the cylinder. Preferably, said hollow cylinder can be made from metal material.

It can be easily understood that one skilled in the art can suitably adjust and modify the specific structures of the sample cell 100 and the base 200 of the sample chamber and the arrangement relationship thereof as needed.

For instance, in a preferred example, the sample cell 100 and the base 200 are both cuboid-shaped, and the dimensions of the receiving portion 111 and the sample cell 100 are designed so that when the sample cell 100 is placed in the receiving portion 111 of the base 200, the sample cell 100 and the base 200 can form a whole cuboid together. In this way, a compact structure can be realized.

In a specific example, the diameter of the viewing hole 110 is selected to be larger than that of the sample cell through-hole 102, and thus the sample can be observed reliably.

Although in the foregoing the present invention is described based on an example of split-type structure, in which the sample chamber comprises one sample cell 100 and one base 200, the invention also covers the example comprising a plurality of sample chambers. That is to say, the sample chamber can comprise one base and a plurality of sample cells which can be used together, and this kind of structure also falls within the scope of the present invention.

Although the invention is described in details with reference to some embodiments, it will be apparent to those skilled in the art that modifications and variations may be made to some features/components/structures of the present invention without departing from the spirit or scope of the invention. In particular, the features disclosed in one embodiment can be combined with those disclosed in other embodiments in arbitrary ways unless the combinations may cause conflicts. It is intended that the present invention covers all the modifications and variations thereof provided they come within the scope of the appended claims and their equivalents.

The invention claimed is:

1. An apparatus for laser ablation analysis of fluid inclusions, comprising:
    a sample cell comprising a sample cell through-hole extending through the sample cell along a first direction, a sample channel extending through the sample cell in a direction transverse to the first direction and fluidly communicating with the sample cell through-hole, and a first transparent element and a second transparent element, each affixed to one end of the sample cell through-hole by a fixing ring; and
    a base comprising a viewing hole and a receiving portion for receiving the sample cell, wherein the viewing hole is coaxially aligned with the sample cell through-hole,
    wherein said sample cell is made from a first material and said base is made from a second material, wherein a density of the second material is less than that of the first material, and/or a coefficient of heat transfer of the second material is greater than that of the first material.

2. The apparatus according to claim 1, characterized in that said first material is stainless steel and said second material is aluminum.

3. The apparatus according to claim 1, characterized in that a heating device is arranged inside said base.

4. The apparatus according to claim 3, characterized in that said heating device comprises a heating rod extending along a direction orthogonal to the sample cell through-hole and the sample channel.

5. The apparatus according to claim 4, characterized in that said base is further provided with a thermocouple arranged orthogonal to the heating rod.

6. The apparatus according to claim 1, characterized in that a sealing element is arranged between each of said first and second transparent elements and the sample cell.

7. The apparatus according to claim 6, wherein the sealing element is a fluoro-rubber sealing ring.

8. The apparatus according to claim 1, characterized in that each of said first and second transparent elements is a quartz glass plate.

9. The apparatus according to claim 1, characterized in that said receiving portion is a step, a through groove, or a recess.

10. The apparatus according to claim 1, having a shape of a cuboid.

11. The apparatus according to claim 1, characterized in that the diameter of said viewing hole is equal to or greater than that of said sample cell through-hole.

12. The apparatus according to claim 1, characterized in that a threaded ferrule is provided at each of two ends of said sample channel for receiving a sample line.

13. The apparatus according to claim 1, characterized in that said sample cell through-hole is configured to receive a hollow cylinder, wherein the external diameter of the hollow cylinder matches the inner diameter of the sample chamber.

14. A device for laser ablation analysis of fluid inclusions, comprising the sample cell according to claim 1, a laser source providing a laser beam, and a light source providing a viewing light beam, wherein the laser beam enters the sample cell through the first transparent element and the viewing light beam enters the sample cell through the second transparent element.

* * * * *